(12) United States Patent
McCarthy et al.

(10) Patent No.: US 6,755,798 B2
(45) Date of Patent: Jun. 29, 2004

(54) PNEUMATIC ACHILLES SLEEVE

(75) Inventors: Fabian McCarthy, Basking Ridge, NJ (US); David C. Hargrave, Madison, NJ (US)

(73) Assignee: Aircast, Inc., Summit, NJ (US)

( * ) Notice: Subject to any disclaimer, the term of this patent is extended or adjusted under 35 U.S.C. 154(b) by 94 days.

(21) Appl. No.: 10/074,960

(22) Filed: Feb. 13, 2002

(65) Prior Publication Data

US 2003/0153857 A1 Aug. 14, 2003

(51) Int. Cl.[7] ................................................ A61F 5/00
(52) U.S. Cl. ........................... 602/13; 602/27; 602/65; 128/882; 128/DIG. 20
(58) Field of Search ................................ 128/846, 869, 128/882, DIG. 20; 602/23, 13, 26, 27, 60, 61, 62, 65

(56) References Cited

U.S. PATENT DOCUMENTS

| 5,288,286 A | * | 2/1994 | Davis .............................. 602/6 |
| 5,314,455 A | * | 5/1994 | Johnson ....................... 607/104 |
| 5,464,385 A |   | 11/1995 | Grim |
| 5,822,887 A | * | 10/1998 | Turner ............................. 36/88 |
| 5,868,690 A | * | 2/1999 | Eischen ........................ 602/13 |
| 6,228,044 B1 |   | 5/2001 | Jensen et al. |
| 6,669,660 B2 |   | 12/2003 | Branch |

FOREIGN PATENT DOCUMENTS

WO     WO 98/19638    * 5/1998

* cited by examiner

Primary Examiner—Michael A. Brown
(74) Attorney, Agent, or Firm—Ropes & Gray LLP

(57) ABSTRACT

The pneumatic Achilles sleeve assembly comprises a sleeve and at least one strap for fastening the sleeve around the ankle. The sleeve assembly positions an arch cell which contains a dynamic volume of air within the sleeve under a human foot. The arch cell is fabricated from a flexible material and is in communication with a conduit member. Upon application of external pressure to the arch cell, air is expelled from said air cell through said conduit member. The sleeve assembly also positions a tendon cell which contains a dynamic volume of air within the sleeve against the Achilles tendon. The tendon cell is in communication with the arch cell via the conduit member. The tendon cell is also fabricated from a flexible material. Upon the expelling of air from said arch cell, the air enters through the conduit member into the tendon cell which exerts a greater pressure against the Achilles tendon.

47 Claims, 8 Drawing Sheets

US 6,755,798 B2

PNEUMATIC ACHILLES SLEEVE

BACKGROUND OF THE INVENTION

1. Field of the Invention

This invention relates to a compression sleeve for pneumatically applying dynamic pressure to the Achilles tendon, and to the sole of the foot, particularly at the arch.

2. Description of Related Art

Active people commonly experience the ache and debilitating effects of posterior heel pain as a result of three commonly accepted causes: Haglund syndrome, Achilles tendinitis/osis and Sever's disease.

Haglund syndrome is characterized by a painful soft tissue swelling where the Achilles tendon attaches to the calcaneum (heel bone). Haglund syndrome can often result in the development of a bony deposit on the back of the calcaneum or in the inflammation of the bursa, the fluid filled sac that decreases friction between the Achilles tendon and the calcaneum, which is known as retrocalcaneal bursitis. It is believed that Haglund syndrome results from the repetitive application of trauma or stress to the Achilles tendon.

Achilles tendinitis and tendinosis describe two classifications of tendon injury around the Achilles tendon. Tendinosis refers to non-inflammatory intratendinous degeneration which is initially asymptomatic. Tendinitis describes symptomatic degeneration of the tendon associated with inflammation. Stanish has referred to these tendon classifications as non-union soft-tissue injuries. It is believed that non-union soft-tissue injuries are caused by inadequate perfusion of the local tissues. The affliction is characterized by soft tissue swelling, tenderness to the touch and roughening about the Achilles tendon known as crepitus. Those suffering from Achilles tendinitis/osis also experience pain with active pointing and passive raising of the foot.

Sever's disease results from a sclerosis or thickening and irregularity of the growth plate known as the calcaneal apophysis. It is believed that Sever's disease results from inflammation of the soft tissues of the heel following an injury. Sever's disease may cause a number of conditions including retrocalcaneal bursitis, traction apophysitis, which is the separating of the tendon from the bone, and osteochondrosis of the calcaneal apophysis which is irritation and inflammation of the bone and cartilage in the heel. Those suffering from Sever's disease experience pain down the back of the heel with passive raising of the foot, rapid and repetitive pointing of the foot and a springy gait. Sever's disease is aggravated by running and jumping.

These conditions are often treated by use of heel lifts which normally are foam pads approximately 0.25 inches thick; oral pain relievers; shoe inserts; anti-inflammatory medications; rest; ultrasound; various physical therapy treatments; and flexibility exercises. Surgical procedures such as diagonal removal of a heel bone known as oblique calcaneal osteotomy; removal of a deep and superficial retrocalcaneal bursae; cleaning and tendon repair are sometimes required for effective treatment.

Plantar fasciitis is an inflammation of the fascia along the bottom of the foot. The fascia are sheets of fibrous tissue beneath the surface of the skin that enclose muscles or muscle groups and separate muscular layers. Plantar faciitis can be quite painful to an individual but can be soothed by massages that increase circulation to the plantar fascia.

U.S. Pat. No. 4,841,957 in the name of Wooten, et al. describes a U-shaped pad for applying compression around the affected area of the heel. However, the device disclosed in the Wooten patent only applies static pressure to the affected area of the Achilles tendon. We have reason to believe that a dynamic pulsating pressure would be more effective in remedying maladies associated with the Achilles tendon.

Nitric oxide is known to be released with a change in sheer stress in blood flow against the endothelial cells lining the veins. Our studies indicate that pulsating pressure accelerates venous velocity. Other studies show that acceleration of venous velocity increases sheer stress. A recent study, *Modulation of Tendon Healing by Nitric Oxide*, authored by George A. C. Murrell and others indicates that nitric oxide is present during tendon healing, and that the inhibition of nitric oxide reduces the healing response. While the tendons are avascular, the small nitric oxide molecule is known to pass through vessel walls. Nitric oxide acts as a vasodilator, providing greater fluid and nutrition to local tissues.

The results indicated by testing the present invention supports the belief that application of a dynamic, pulsating pressure around the sides of the Achilles tendon provides relief and healing to those suffering from maladies afflicting the Achilles tendon.

United Kingdom patent No. 817,521 discloses an apparatus for facilitating the blood circulation in the extremities of the human body. The device shown in this patent is cumbersome, making the same difficult and time consuming to attach to the lower leg of the wearer. A further disadvantage in the use of this device resides in the fact that the inflatable cushions must be inflated from an external source, such as a pump.

U.S. Pat. No. 5,348,530 discloses a pneumatic ankle brace with a bladder and foot pump arrangement. The device of this patent is of rather complicated construction and requires use of a detachable hand-held pump.

U.S. Pat. No. 4,841,956 discloses a device adapted to be mounted to the lower leg and foot of a person for inducing venous blood flow in the leg. This device includes a pulse generator and programmable distributor necessitating a non-ambulatory position for the wearer during use.

U.S. Pat. No. 4,678,945 discloses a self-inflating ankle brace including air bags with resilient, compressible filler material. This patent discloses only a brace.

U.S. Pat. No. 6,322,530, assigned to the instant assignee and incorporated herein by reference in its entirety, discloses a wrap made of a plurality of stretchable flexible straps. The straps wrap around the foot to hold in place one aircell positioned in the vicinity of the Achilles tendon and another aircell positioned in the vicinity of the arch of the foot, the two aircells being operatively connected to one another through a conduit member. As the user walks and steps on the aircell at the arch, that aircell is compressed, and the pressure in the aircell at the Achilles tendon is increased. As the user step off the arch aircell, the airflow is reversed, and air travels back from the Achilles tendon aircell to the arch aircell, ready for the next cycle. This device provides effective pneumatic compression of the Achilles tendon, but can be difficult for the user to apply and adjust properly.

SUMMARY OF THE INVENTION

The present invention provides relief to those who are suffering from posterior heel pain or from plantar faciitis.

Therefore, an object of the invention is to provide an Achilles sleeve which includes a device for applying pulsating pressure to the Achilles tendon and to the arch area of the foot.

Another object of the invention is to utilize a foot cell to pulse pump pressure to the area around the Achilles tendon.

A further object of the invention is to provide an Achilles sleeve assembly that provides pulsating pressure to the Achilles tendon by use of a aircell that envelopes the Achilles tendon.

An even further object of the invention is to provide an Achilles sleeve assembly having a flexible stretchable sleeve with an inelastic strap around the ankle area to facilitate positioning of the sleeve on the foot and ankle.

The foregoing advantages are achieved by the pneumatic Achilles sleeve assembly of the present invention. The Achilles sleeve assembly comprises a sleeve, the sleeve comprising a foot portion that envelopes the circumference of the foot in the area of the arch of the foot, and an ankle portion that can be opened and closed at the ankle by means of an inelastic strap to allow easy entry of the foot into the sleeve. The foot portion includes a pocket on the inner surface thereof disposed against the arch of the foot, the pocket being configured to accommodate an arch cell that contains a dynamic volume of air. The arch cell is fabricated from a flexible material and is operatively connected to a conduit member. The tendon cell is shaped to envelop the sides of the Achilles tendon and is disposed on the rear inner surface of the ankle portion of the sleeve. The tendon cell also is operatively connected to the conduit member. Upon application of external pressure to the arch cell, air is expelled from the arch cell through the conduit member and into the tendon cell.

Both the tendon cell and the arch cell are fabricated from a flexible material defining pockets containing open-cell foam pads. When air is expelled from said arch cell, the air passes through the conduit member into the tendon cell which exerts a greater pressure against the Achilles tendon. The arch and tendon cells are self-inflating. Thus, an external pump is not required.

A better understanding of the present invention and its objects and advantages can be had by making reference to the following detailed description taken in conjunction with the accompanying drawings.

BRIEF DESCRIPTION OF THE DRAWINGS

The drawings which are part of the disclosure illustrate the instant invention.

DETAILED DESCRIPTION OF THE INVENTION

The following is a description of a preferred embodiment of the instant invention.

Figure 4:
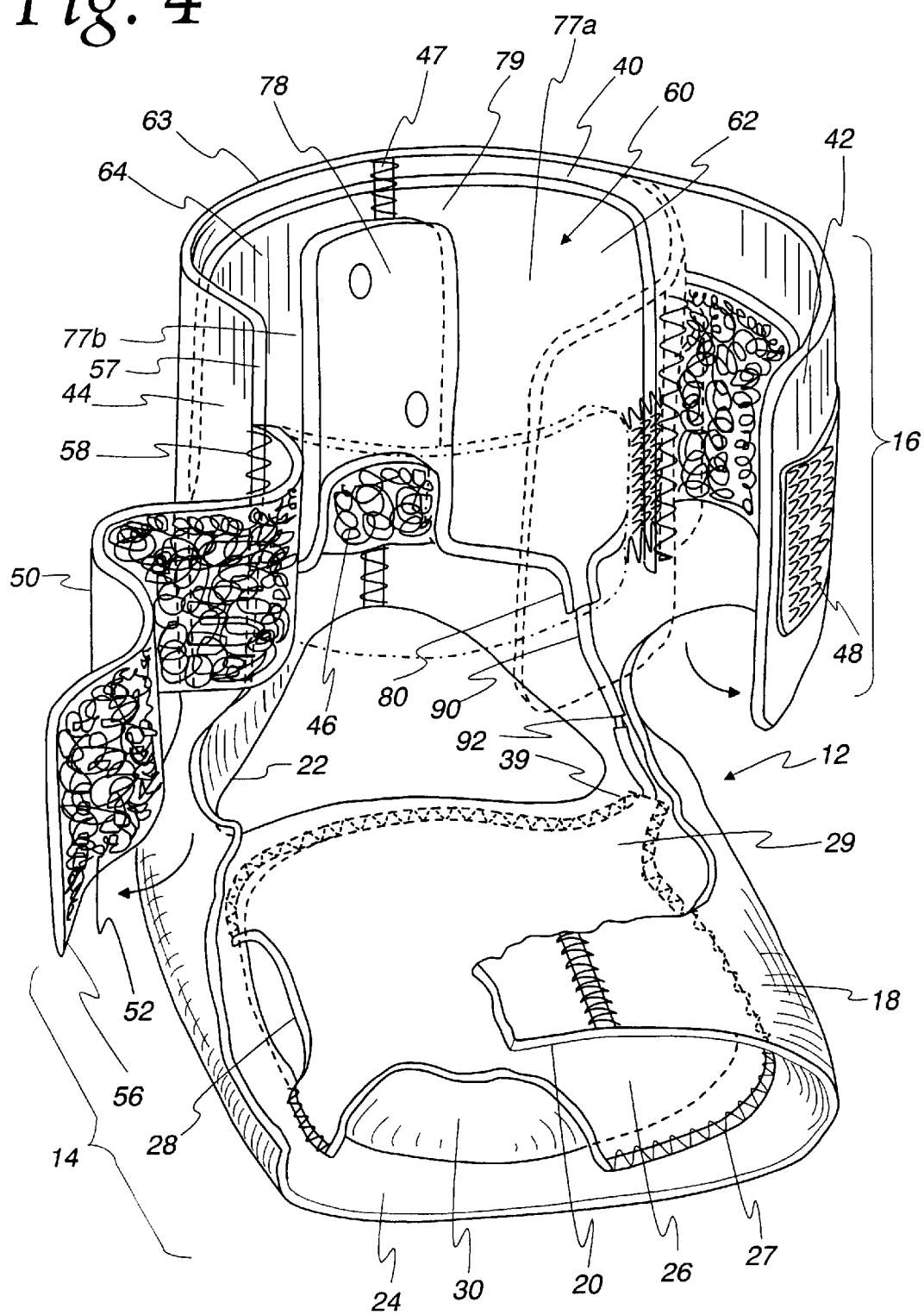
FIG. 4 is a perspective view of the sleeve assembly of the instant invention in which the ankle strap is open.

The instant invention comprises a sleeve assembly that accommodates a pneumatic system. FIG. 4 depicts the sleeve assembly 10 of the present invention that can be worn on either foot of a human being. The sleeve assembly 10 comprises a sleeve 12 preferably made of a flexible stretchable material, such as neoprene. Sleeve 12 comprises a foot portion 14 and an ankle portion 16.

Figure 1:
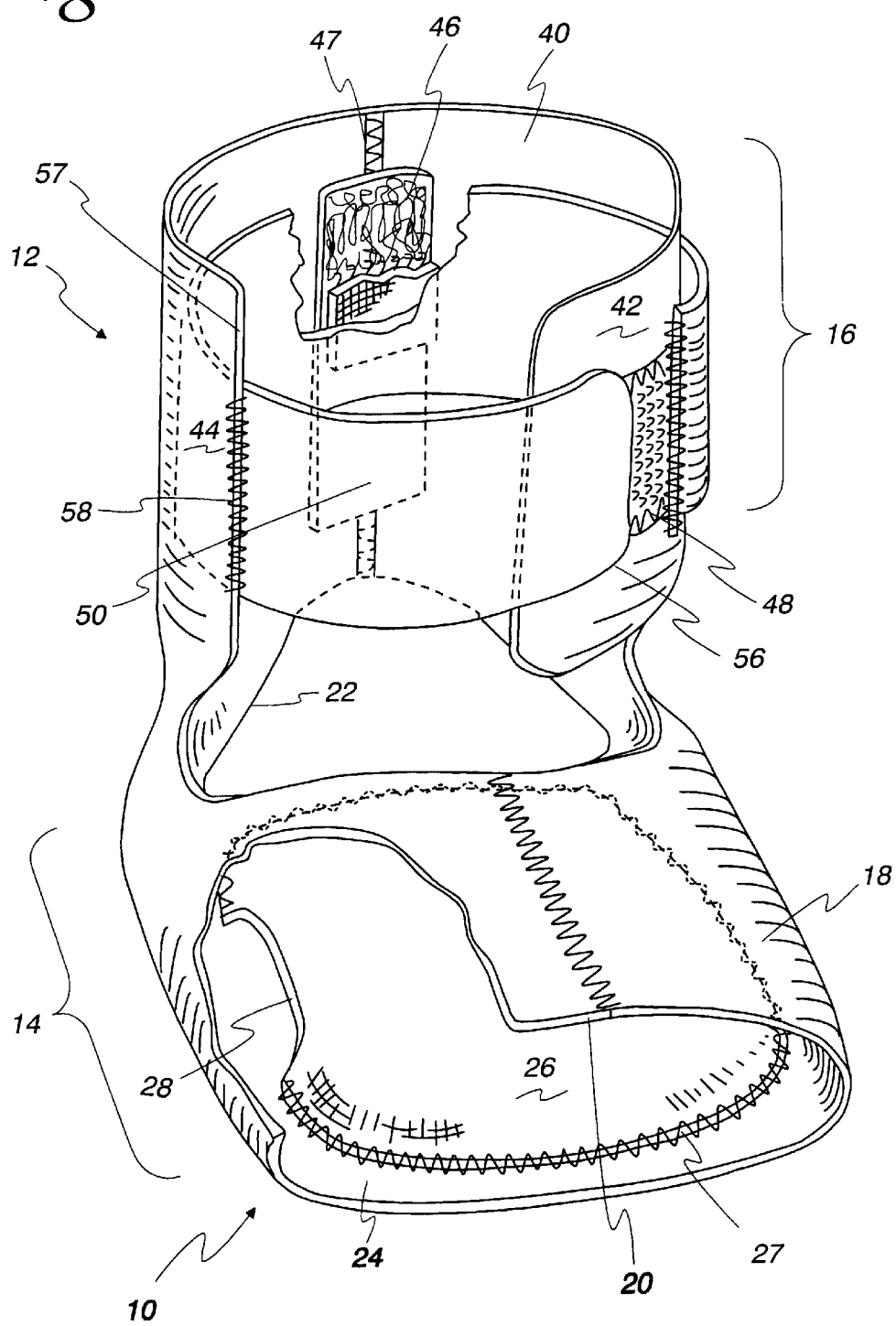
FIG. 1 is a perspective view of the sleeve of the instant invention.
Figure 2:
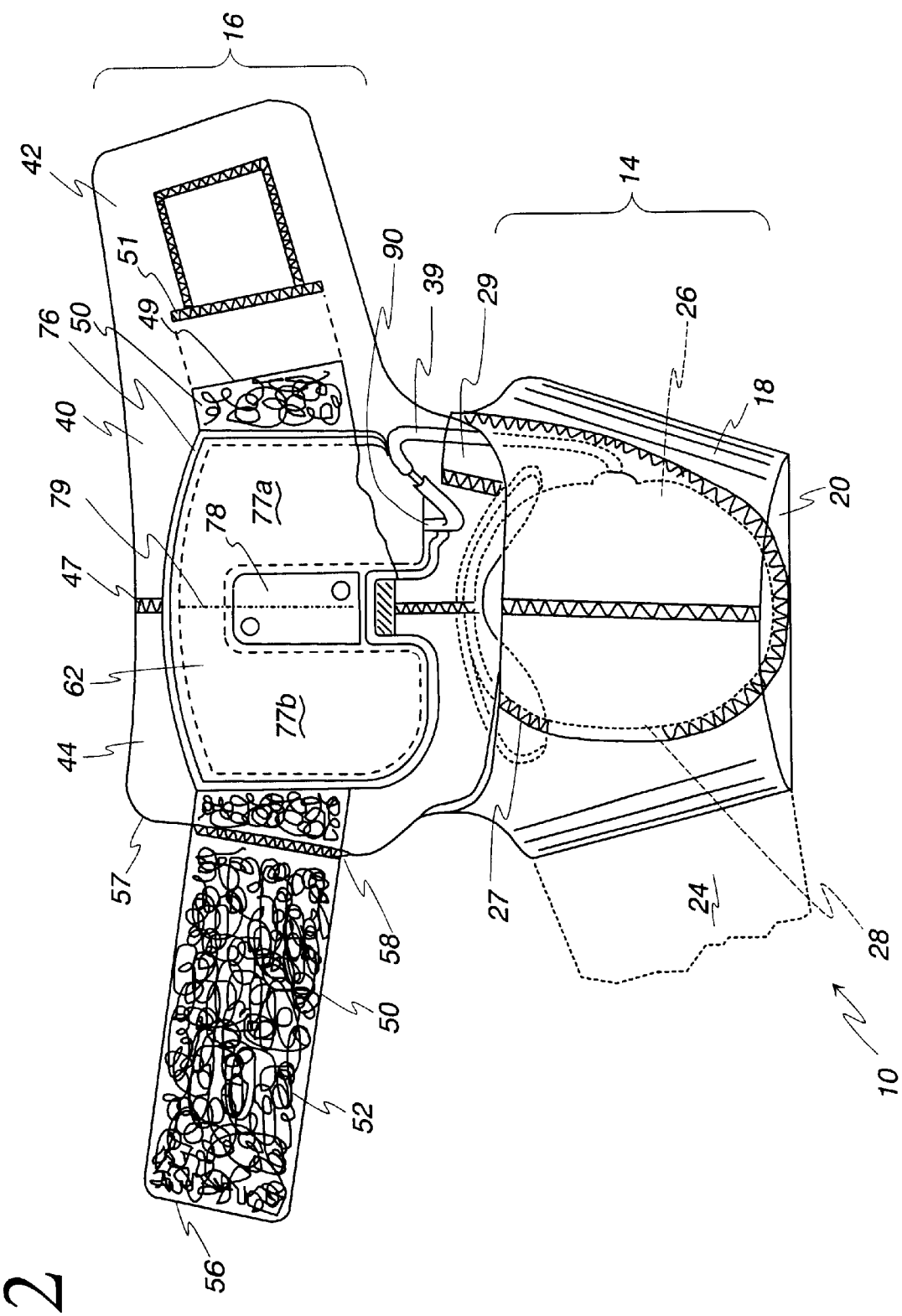
FIG. 2 is a plan view of the sleeve assembly of the invention showing the aircells connected by the conduit and showing the strap.
Figure 3:
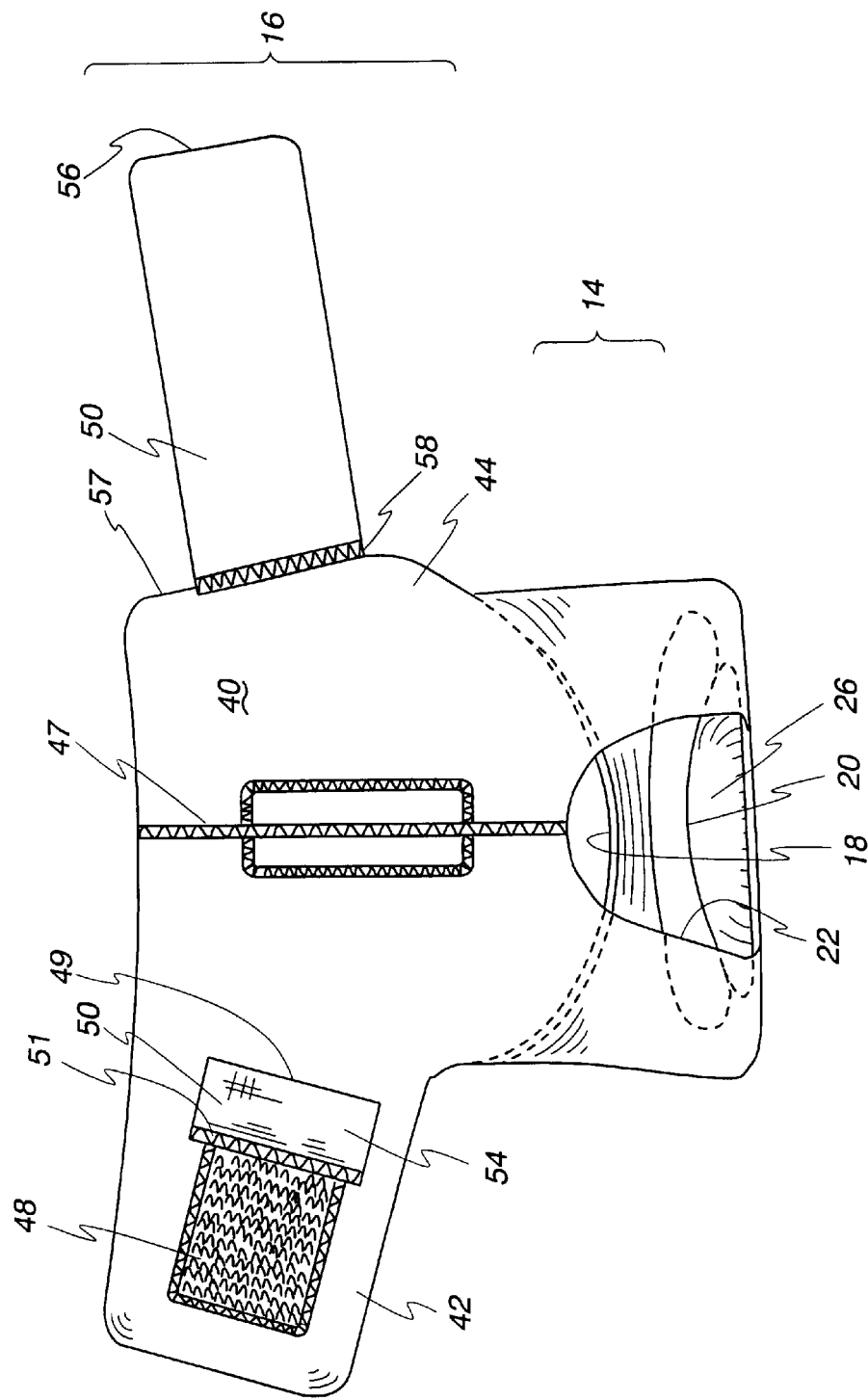
FIG. 3 is a rear view of the sleeve of the instant invention in which the strap is open.

As shown in FIG. 1, foot portion 14 is in the form of a cuff 18 that surrounds the circumference of the foot in the region of the arch. The cuff 18 has a distal end 20 which is in the form of an opening through which the forefoot extends, and a proximal end 22 that defines an opening through which the heel of the foot extends. The inner surface 24 of cuff 18 has a pocket 26 provided thereon so as to be juxtaposed against the arch of the foot when the sleeve assembly is applied to a user. The pocket 26 is configured to receive aircell 30, described in greater detail below. Pocket 26 can be attached by peripheral seam 27 to surface 24 by known means such as stitching, gluing, or welding. Pocket 26 can be made of a neoprene foam thicker than the neoprene of sleeve 12 to further promote comfort for the user. In one embodiment, seam 27 will have a gap 28 along one side of sufficient size to allow aircell 30 to be inserted into pocket 26, so that aircell 30 need not be in position when pocket 26 is being stitched, glued, or welded to inner surface 24. A neck portion 29 will be of sufficient size to allow the passage therethrough of the air conduit member, described below.

Figure 5:
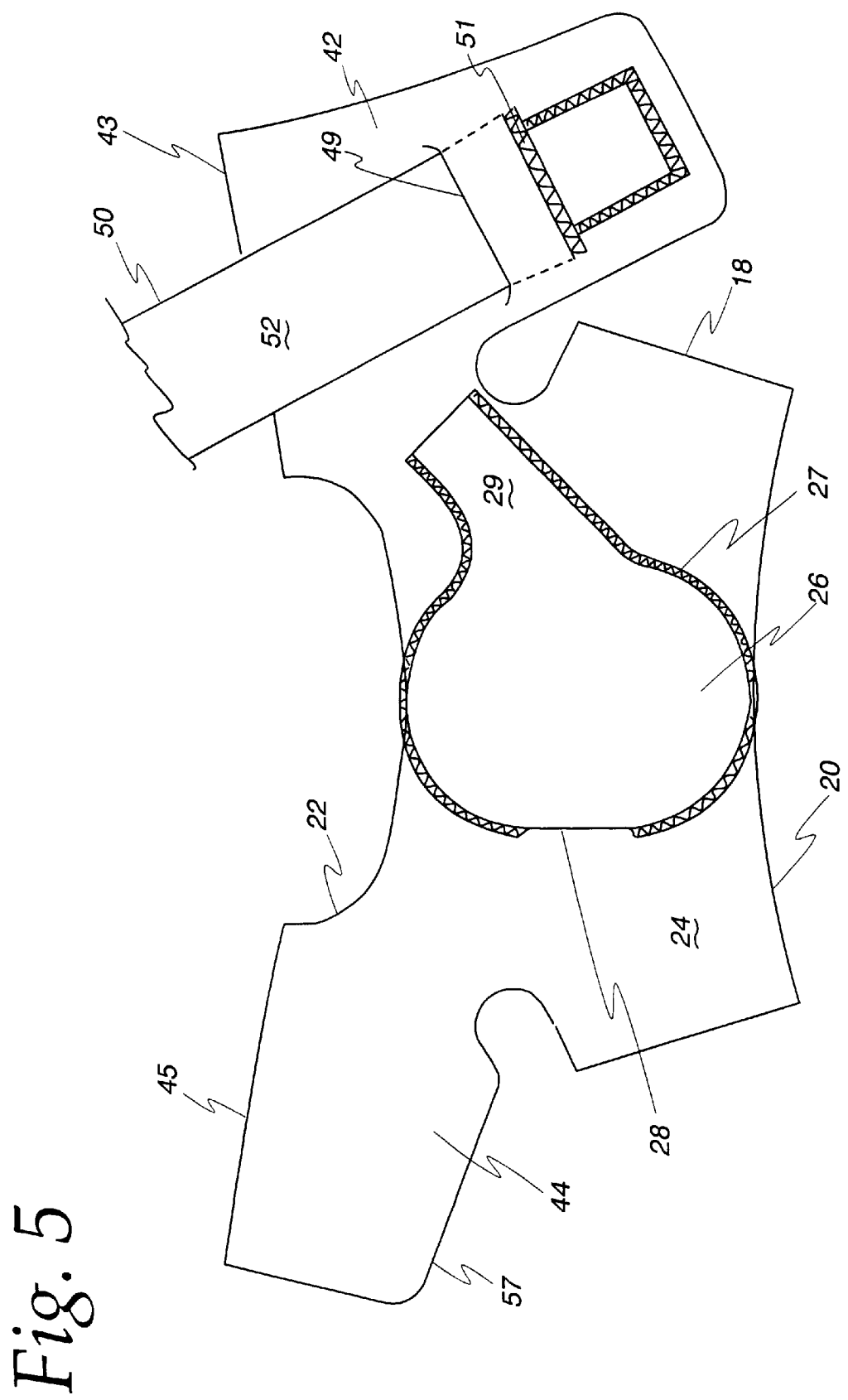
FIG. 5 is a plan view of the fabric blank used to form the sleeve of the instant invention.
Figure 6:
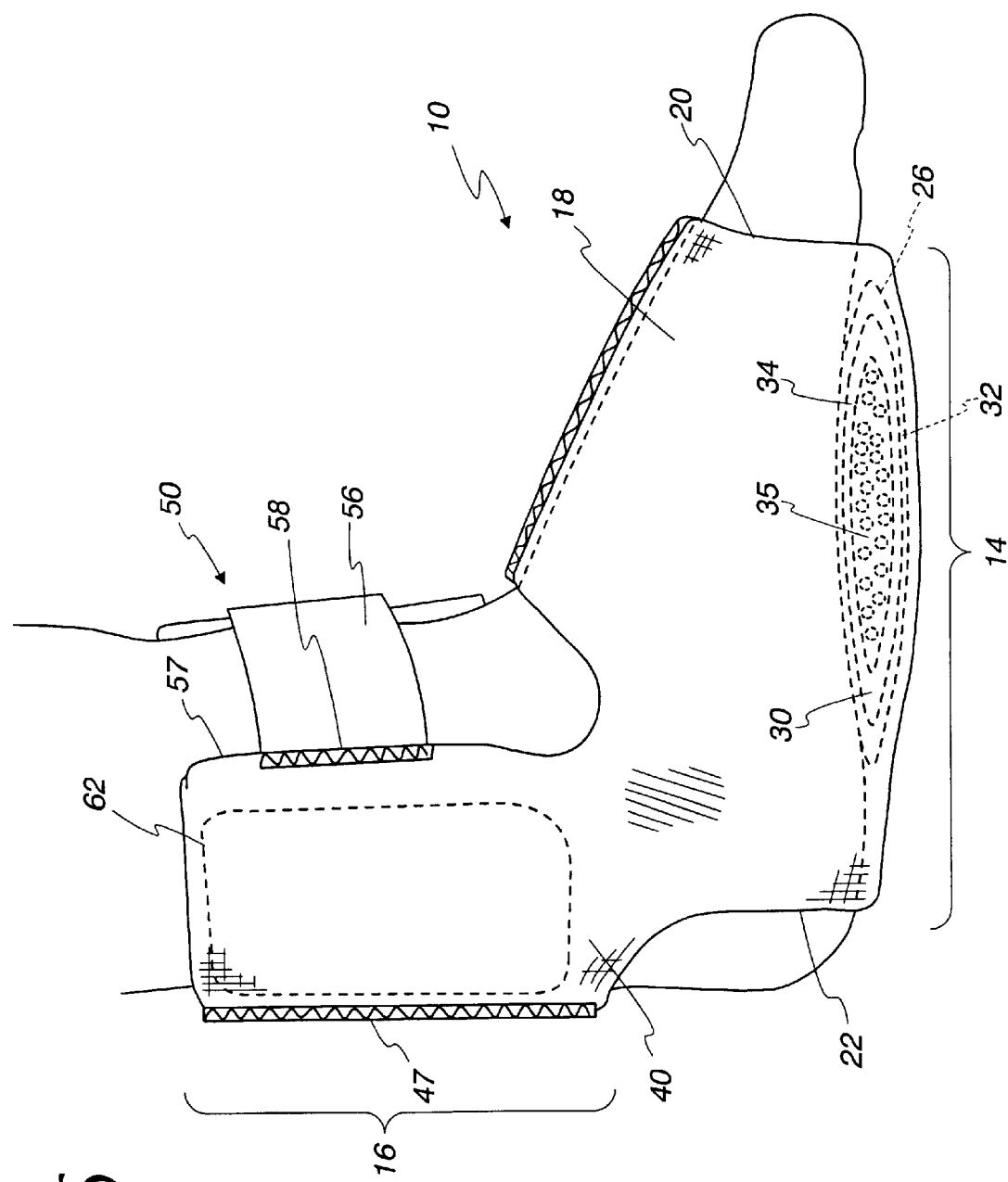
FIG. 6 is a side view of the present invention placed on a human foot with the pneumatic system in partial phantom.

Ankle portion 16 of sleeve 12 includes a rear portion 40 that covers the posterior surface of the ankle region including the Achilles tendon, and first and second side flaps 42, 44 extending laterally from either side of said rear portion 40. First and second side flaps 42 and 44 wrap around the front of the user's ankle when the sleeve assembly is in place on a user. FIG. 5 illustrates the blank from which sleeve 12 can be made. It may be seen that each of first and second side flaps 42 and 44 terminates at inner edges 43 and 45 respectively. These edges 43 and 45 are fastened together by stitching, welding, gluing, or other known means to form a seam 47 that runs vertically along the back of the user's ankle when the sleeve assembly 10 is in position on a user. A strip of fastening material 46 is disposed on the inner surface of rear portion 40 in the general area of the Achilles tendon. Hook or loop material sold under the trademark VELCRO® can be used for this purpose. A second patch of hook or loop material 48 is affixed to the outer surface of first side flap 42. It is preferred that hook bearing material be used for both strip 46 and patch 48.

The sleeve assembly of the instant invention further comprises an ankle strap 50 formed of an inelastic material and having a plurality of hooks or loops on one side thereof. If patch 48 comprises hooks, then strap 50 will comprise loops 52. Strap 50 has a first end 54 fixedly secured to the outer surface of first side flap 42, rearward of second patch 48. First end 54 of strap 50 can be secured to the outer surface of first side flap 42 at securement site 51 by known means such as stitching, gluing, or welding. First side flap 42 has a slit 49 disposed rearward of the site of securement 51 of first strap end 54 to first side flap 42. Slit 49 is long enough to allow the width of strap 50 to pass therethrough.

Figure 7:
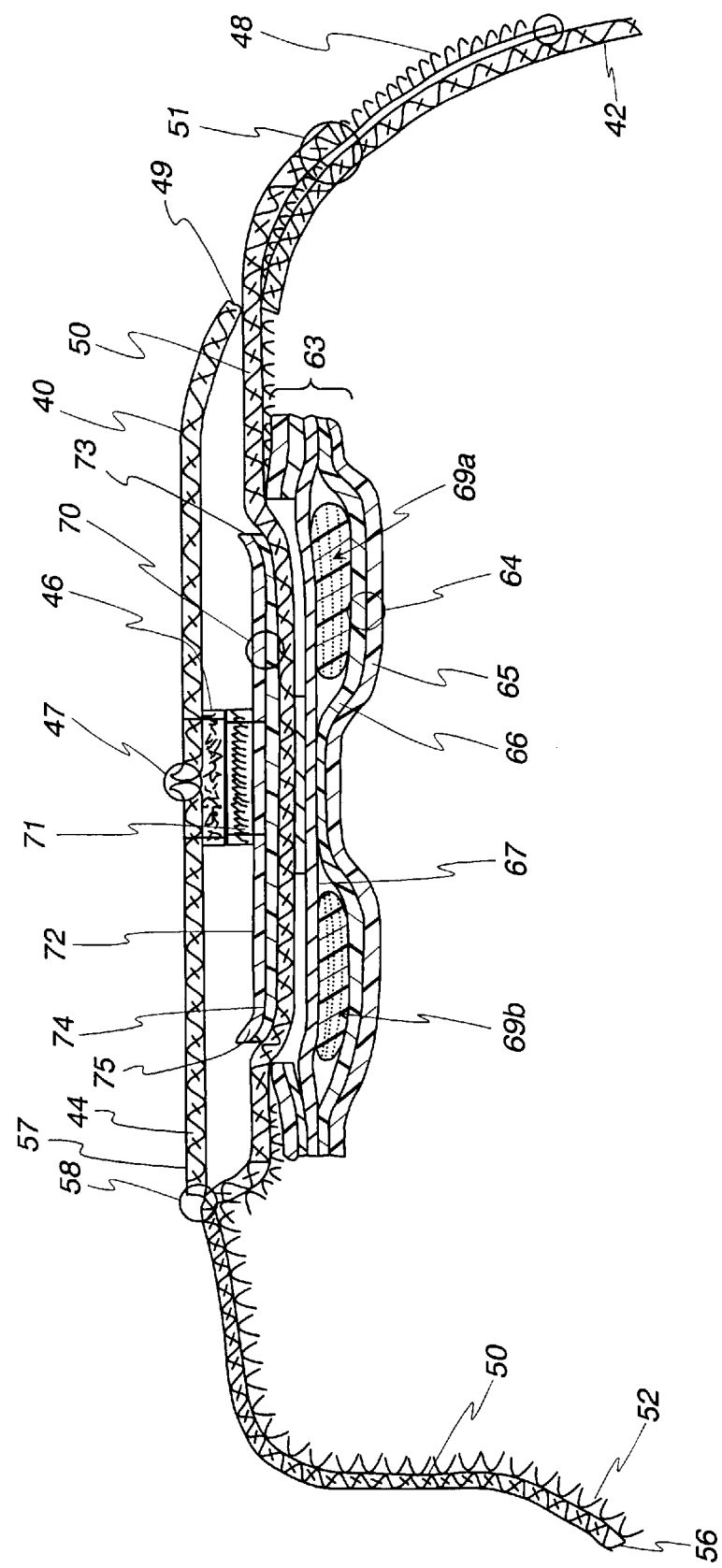
FIG. 7 is a cross-sectional view taken along line 7—7 in FIG. 2 showing the Achilles tendon cells, the strap and the ankle portion of the sleeve assembly.

The sleeve assembly of the instant invention further comprises a pneumatic system 60 comprising arch aircell 30, described in more detail below, and tendon aircell 62. In the illustrated embodiment, tendon aircell 62 is generally in the shape of an inverted "U", with two downwardly extending compartments 77a, 77b and a central portion 78 therebetween. As best shown in FIG. 7, tendon cell 62 comprises a first wall 64 and a second wall 67 each made of plastic.

First wall 64 is preferable made of nylon ply 65 coated on one surface with polyurethane 66; in the construction of the tendon cell of the instant invention, the nylon side forms an exterior surface of the cell and the polyurethane is on an inside surface. Second wall 67 can be formed of polyurethane. Pieces of open-cell foam material 69a, 69b of about 0.2 inches thick are disposed between first wall 64 and second wall 67 in each of the compartments 77a, 77b. A third wall 70 comprises nylon ply 72 and polyurethane coating 74. Third wall 70 is juxtaposed against second wall 67, with polyurethane coating 74 facing polyurethane second wall 67. The three walls 64, 67 and 70 are sealed together along their common edges at edge seal 63, preferably by radio-frequency welding, with one surface of polyurethane wall 67 in contact with polyurethane coating 66, and polyurethane coating 74 in contact with the opposite surface of polyurethane wall 67. The first wall 64, second wall 67, and third wall 70 are also sealed together at central portion 78 of tendon air cell 62, except for one small area extending between the downwardly extending compartments 77a, 77b. This unsealed area forms a channel 79 between the two compartments through which air can flow.

First wall 64, second wall 67, and third wall 70 each have a neck portion in alignment with the others, generally indicated at reference numeral 80 in FIG. 4. The neck portions are sealed together at their edges with a tunnel therebetween for receiving a tendon inlet tube 90. The tendon inlet tube 90 is hermetically secured between the neck portions of first wall 64 and second wall 67, and serves as a duct to bring air into the compartment 77a, through channel 79, and into compartment 77b.

Third wall 70 has two slits 73, 75 therein disposed substantially on either side of tendon aircell 62, each slit 73, 75 being long enough to accommodate the width of strap 50. Strap 50 passes through slit 49 of ankle portion 16 of sleeve 12, then through slit 73 of tendon aircell 62. Strap 50 further extends between second wall 67 and third wall 70, and then through slit 75. Strap 50 then continues along the inner surface of second side flap 44, and is fixedly attached to outer edge 57 of second side flap 44 at attachment site 58. The attachment between strap 50 and side flap 44 can be made by stitching, gluing, welding, or other known means. The second end 56 of strap 50 extends beyond attachment site 58, for engagement with patch 48 on first flap 42. Third wall 70 of tendon cell 62 also has on its outer surface a strip of hook and loop material 71 sized and positioned to engage hook and loop strip 46 on the inner surface of ankle portion 40.

The arch cell 30 comprises two generally oval or elliptical walls, a bottom wall 32 and a top wall 34, each preferably made of nylon coated on one side with polyurethane. The walls 32 and 34 are placed in registry with the polyurethane coated surfaces facing one another, and are sealed to one another around the edges thereof to provide a hermetically sealed aircell. The aircell 30 contains a piece of open-cell foam 35 of about 0.5 inches thick. The foam pad 35 is self-inflating, as disclosed in U.S. Pat. No. 4,628,945, which is assigned to the assignee herein and incorporated herein by reference.

The base wall 32 and the top wall 34 of arch cell 30 each has corresponding neck portions sealed to each other with a tunnel therein to form neck 29 for hermetically receiving outlet tube 39. The outlet tube 39 is removably coupled by a connector 92 to inlet tube 90 to provide an air-tight pneumatic system comprising the arch cell 30, the tendon cell 62, and the connecting conduit.

When weight from the user's foot bears upon arch cell 30, air is quickly expelled from the arch cell 30 to the tendon cell 62 to increase the pressure on the Achilles tendon. When weight on the arch cell 30 is removed, the self-inflating foam piece 35 in the arch cell 30 expands the walls 32, 34 of the arch cell 30 to increase the volume of the arch cell. The increased volume creates a vacuum which quickly sucks air from the tendon cell 62 back into the arch cell 30 thereby decreasing the pressure that the tendon cell 62 bears on the Achilles tendon.

Figure 8:
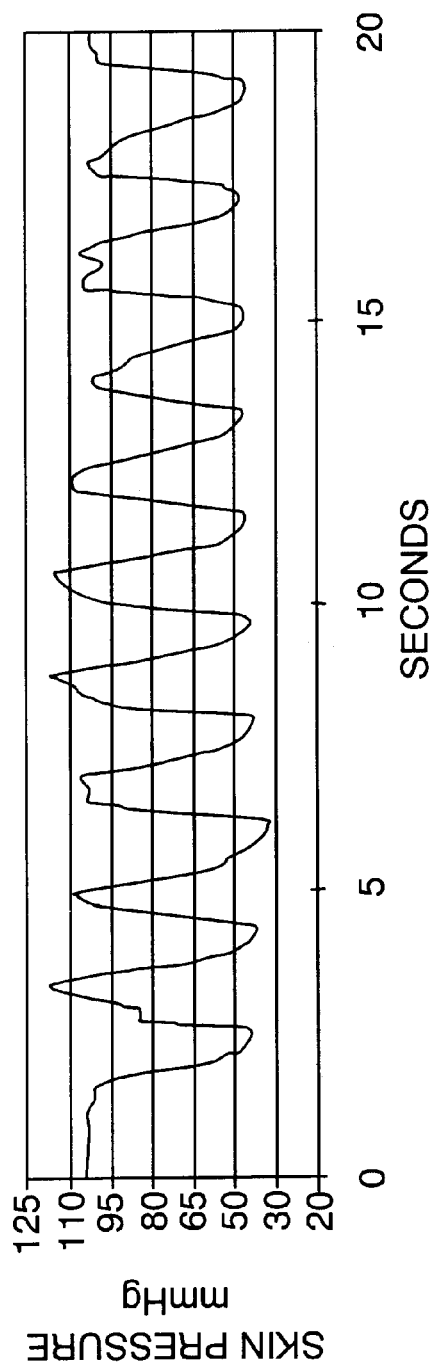
FIG. 8 is a graph of the pulsating pressure the instant invention applies to the Achilles tendon.

Walking while wearing the pneumatic Achilles sleeve assembly 10 of the instant invention produces a rapid change in pressure which enhances the magnitude of the pulsation on the sides of the heel, thereby increasing the velocity of blood flow in the foot and the leg. This results in an increase in vascular shear stress and, we believe, the release of nitric oxide. Hence, the pulsating compression at the sides of the heel may enhance diffusion of nitric oxide into the Achilles tendon. The pulsating pressure applied by the tendon cell 62 to the tendon is shown in FIG. 8. The abscissa represents skin pressure in mmHg; the ordinate represents walking time in seconds.

The arch cell 30 fits into the arch of the foot between the tarsal head and the calcaneus metatarsal. Confining the arch cell 30 to this portion of the foot facilitates insertion of the foot with the sleeve assembly 10 into the wearer's shoe and permits the arch cell 30 to function as a dynamic orthotic comfortably supporting the arch with resilient pressure. We believe that the arch cell 30 under the arch also acts as a dynamic pump enhancing the flow of blood in the foot and leg, which may well be a source of nitric oxide. The pulsating pressure to the arch of the foot may also provide treatment for plantar fasciitis.

The tendon cell 62 envelops the back of the heel and thus the Achilles tendon. The inflation of the tendon cell 62 is confined to the inflatable compartments 77a, 77b. The inflation of the tendon cell 62 is confined by the inelastic strap 50 that extends behind the tendon cell 62 and is secured fixedly in place by the user by attachment of loops 52 to patch 48, thus preventing outward expansion of the tendon cell and directing the energy of pulsation inwardly to the sides of the Achilles tendon.

The pressure from the Achilles tendon cell 62 is confined to the sides of the Achilles tendon rather than the back of the Achilles tendon by dividing the tendon cell 62 into two compartments 77a, 77b separated by a medial uninflated zone 78. Both of the compartments 77a and 77b are inflated with air flowing from inlet tube 90 into compartment 77a, through channel 79, and into compartment 77b. Without the uninflated central portion 78, inflation could cause the second and third cell walls 67 and 70 to push away from the heel. Under such conditions, pressure against the sides of the Achilles tendon would be lost.

To use the Achilles sleeve assembly 10 of the instant invention, the first and second side flaps 42, 44 are opened and separated. The user puts the foot into the sleeve 12 through cuff 18 until arch cell 30 is positioned beneath the user's arch. The first side flap 42 is folded over the front of the user's ankle. The second side flap 44 is folded over the front of the user's ankle and, depending on its length and the size of the user's ankle, over first side flap 42. The loop-bearing side 52 of strap 50 is pressed in place against patch 48 on the outside of first flap 42 to secure the sleeve assembly in place. When this is done, the tendon cell 62 will be correctly positioned against the Achilles tendon without any additional adjustment by the user. Further, arch cell outlet tube 39 and tendon cell inlet tube 90 will already be connected by connector 92 and in their proper positions.

Although no further adjustment of the pneumatic system is required, the tubes can be disconnected at connector 92 to adjust the pressure in the system and then reconnected, as may be desirable for certain users, or under certain conditions such as high altitudes.

It will be appreciated that the detailed description and the examples relate to the preferred embodiment by way of example only. Many variations of the invention will be obvious to those knowledgeable in the field, and such obvious variations are within the scope of the invention as described and claimed, whether or not expressly described.

What is claimed is:

1. A pneumatic sleeve assembly for applying dynamic pressure to the Achilles tendon of a human foot, the sleeve assembly comprising a sleeve adapted to envelop a portion of the ankle and a portion of the foot, the sleeve comprising an ankle portion extending from the region of the ankle above the Achilles tendon to the foot and a substantially tubular foot portion surrounding the circumference of the foot in the region of the arch, an arch cell containing a volume of air positioned within said foot portion of said sleeve so as to be located under the arch of the foot, said arch cell being in communication with a conduit member, said arch cell being fabricated from a flexible material, so that upon application of external pressure to said arch cell air is expelled through said conduit member;

an Achilles tendon cell containing a volume of air, said tendon cell being operatively connected to said arch cell via said conduit member, said tendon cell being positioned within said ankle portion of said sleeve so as to be located against the Achilles tendon, said tendon cell being fabricated from a flexible material, so that upon expelling of air from said arch cell through said conduit member into said tendon cell, said tendon cell exerts a dynamic pressure against the Achilles tendon; and means for opening and releasably closing said ankle portion to facilitate application and removal of said assembly on the human.

2. The sleeve assembly of claim 1 wherein said arch cell contains a foam pad whereby upon removal of said exterior pressure from said arch cell, air is drawn from said tendon cell through said conduit member into said arch cell.

3. The sleeve assembly of claim 1 wherein said tendon cell includes a hermetically sealed chamber for positioning on at least one side of the Achilles tendon.

4. The sleeve assembly of claim 3 wherein said tendon cell further includes a noninflatable medial zone for positioning on the back of the Achilles tendon.

5. The sleeve assembly of claim 1 wherein said tendon cell comprises two walls sealed together along common edges thereof to form a pocket.

6. The sleeve assembly of claim 1 wherein said means for opening and releasably closing said ankle portion comprises a strap.

7. The sleeve assembly of claim 6 wherein said strap is fabricated from a flexible, inelastic material which is releasably engageable by a plurality of hooks.

8. The sleeve assembly of claim 7 wherein said strap comprises a woven filament material.

9. The sleeve assembly of claim 7 wherein said strap has a first end, a medial portion and a second end, and said ankle portion comprises first and second side flaps, said first end of said strap being fixedly attached to said first side flap of said ankle portion, said medial portion of said strap being fixedly attached to said second side flap of said ankle portion, and said second end of said strap being adapted to wrap around the front of the user's ankle.

10. The sleeve assembly of claim 9 further comprising means for releasably attaching said second end of said strap to said first side flap of said ankle portion.

11. The sleeve assembly of claim 10 wherein said releasable attaching means comprises mating hook and loop materials on said second end of strap and said first flap of said ankle portion.

12. The sleeve assembly of claim 5 wherein said tendon cell further comprises a third wall such that said second wall is between said first wall and said third wall, and wherein said sleeve assembly comprises a strap, said third wall comprising means for engaging said strap.

13. The sleeve assembly of claim 12 wherein said means for engaging said strap comprises at least one slit for receiving said strap therethrough.

14. The sleeve assembly of claim 1 wherein said conduit member comprises two tubes connectable together by a coupling member, said first tube is in communication with said arch cell and said second tube is in communication with said tendon cell.

15. The sleeve assembly of claim 1 wherein said tendon cell includes first and second lateral self-inflatable compartments separated by a medial non-inflatable portion.

16. The sleeve assembly of claim 1 further comprising a flexible, inelastic support means disposed behind said tendon cell.

17. The sleeve assembly of claim 16 wherein said means for opening and releasably closing said ankle portion comprises a flexible, inelastic strap, and said support for said tendon cell comprises a portion of said strap.

18. A pneumatic sleeve assembly for applying dynamic pressure to the Achilles tendon of a human foot, the sleeve assembly comprising a sleeve adapted to envelop a portion of the ankle and a portion of the foot, the sleeve comprising an ankle portion extending from the region of the ankle above the Achilles tendon to the foot and a substantially tubular foot portion surrounding the circumference of the foot in the region of the arch, an arch cell containing a volume of air positioned within said foot portion of said sleeve so as to be located under the arch of the foot, said arch cell being in communication with a conduit member, said arch cell being fabricated from a flexible material, so that upon application of external pressure to said arch cell air is expelled through said conduit member;

an Achilles tendon cell containing a volume of air, said tendon cell being operatively connected to said arch cell via said conduit member, said tendon cell being positioned within said ankle portion of said sleeve so as to be located against the Achilles tendon, said tendon cell being fabricated from a flexible material, so that upon expelling of air from said arch cell through said conduit member into said tendon cell, said tendon cell exerts a dynamic pressure against the Achilles tendon; and a flexible, inelastic support means disposed behind said tendon cell.

19. The pneumatic sleeve assembly of claim 18 further comprising means for opening and releasably closing said ankle portion to facilitate application and removal of said assembly on the human.

20. The sleeve assembly of claim 19 wherein said means for opening and releasably closing said ankle portion comprises a flexible, inelastic strap, and said support for said tendon cell comprises a portion of said strap.

21. The sleeve assembly of claim 18 wherein said arch cell contains a foam pad whereby upon removal of said exterior pressure from said arch cell, air is drawn from said tendon cell through said conduit member into said arch cell.

22. The sleeve assembly of claim 18 wherein said tendon cell includes a hermetically sealed chamber for positioning on at least one side of the Achilles tendon.

23. The sleeve assembly of claim 22 wherein said tendon cell further includes a noninflatable medial zone for positioning on the back of the Achilles tendon.

24. The sleeve assembly of claim 18 wherein said tendon cell comprises two walls sealed together along common edges thereof to form a pocket.

25. The sleeve assembly of claim 20 wherein said strap is releasably engageable by a plurality of hooks.

26. The sleeve assembly of claim 20 wherein said strap comprises a woven filament material.

27. The sleeve assembly of claim 20 wherein said strap has a first end, a medial portion and a second end, and said ankle portion comprises first and second side flaps, said first end of said strap being fixedly attached to said first side flap of said ankle portion, said medial portion of said strap being fixedly attached to said second side flap of said ankle portion, and said second end of said strap being adapted to wrap around the front of the user's ankle.

28. The sleeve assembly of claim 27 further comprising means for releasably attaching said second end of said strap to said first side flap of said ankle portion.

29. The sleeve assembly of claim 28 wherein said releasable attaching means comprises mating hook and loop materials on said second end of strap and said first flap of said ankle portion.

30. The sleeve assembly of claim 24 wherein said tendon cell further comprises a third wall such that said second wall is between said first wall and said third wall, and wherein said sleeve assembly comprises a strap, said third wall comprising means for engaging said strap.

31. The sleeve assembly of claim 18 wherein said conduit member comprises two tubes connectable together by a coupling member, said first tube is in communication with said arch cell and said second tube is in communication with said tendon cell.

32. The sleeve assembly of claim 18 wherein said tendon cell includes first and second lateral self-inflatable compartments separated by a medial non-inflatable portion.

33. A pneumatic sleeve assembly for applying dynamic pressure to the Achilles tendon of a human foot, the sleeve assembly comprising
  a sleeve adapted to envelop a portion of the ankle and a portion of the foot, the sleeve comprising an ankle portion extending from the region of the ankle above the Achilles tendon to the foot and a substantially tubular foot portion surrounding the circumference of the foot in the region of the arch,
  an arch cell containing a volume of air positioned within said foot portion of said sleeve so as to be located under the arch of the foot, said arch cell being in communication with a conduit member, said arch cell being fabricated from a flexible material, so that upon application of external pressure to said arch cell air is expelled through said conduit member; and
  an Achilles tendon cell containing a volume of air, said tendon cell being operatively connected to said arch cell via said conduit member, said tendon cell being positioned within said ankle portion of said sleeve so as to be located against the Achilles tendon, said tendon cell being fabricated from a flexible material, so that upon expelling of air from said arch cell through said conduit member into said tendon cell, said tendon cell exerts a dynamic pressure against the Achilles tendon.

34. The pneumatic sleeve assembly of claim 33 further comprising means for opening and releasably closing said ankle portion to facilitate application and removal of said assembly on the human.

35. The sleeve assembly of claim 34 wherein said means for opening and releasably closing said ankle portion comprises a flexible, inelastic strap, a portion of said strap extending behind said tendon cell.

36. The sleeve assembly of claim 33 wherein said arch cell contains a foam pad whereby upon removal of said exterior pressure from said arch cell, air is drawn from said tendon cell through said conduit member into said arch cell.

37. The sleeve assembly of claim 33 wherein said tendon cell includes a hermetically sealed chamber for positioning on at least one side of the Achilles tendon.

38. The sleeve assembly of claim 37 wherein said tendon cell further includes a noninflatable medial zone for positioning on the back of the Achilles tendon.

39. The sleeve assembly of claim 33 wherein said tendon cell comprises two walls sealed together along common edges thereof to form a pocket.

40. The sleeve assembly of claim 35 wherein said strap is releasably engageable by a plurality of hooks.

41. The sleeve assembly of claim 35 wherein said strap comprises a woven filament material.

42. The sleeve assembly of claim 35 wherein said strap has a first end, a medial portion and a second end, and said ankle portion comprises first and second side flaps, said first end of said strap being fixedly attached to said first side flap of said ankle portion, said medial portion of said strap being fixedly attached to said second side flap of said ankle portion, and said second end of said strap being adapted to wrap around the front of the user's ankle.

43. The sleeve assembly of claim 42 further comprising means for releasably attaching said second end of said strap to said first side flap of said ankle portion.

44. The sleeve assembly of claim 43 wherein said releasable attaching means comprises mating hook and loop materials on said second end of strap and said first flap of said ankle portion.

45. The sleeve assembly of claim 39 wherein said tendon cell further comprises a third wall such that said second wall is between said first wall and said third wall, and wherein said sleeve assembly comprises a strap, said third wall comprising means for engaging said strap.

46. The sleeve assembly of claim 33 wherein said conduit member comprises two tubes connectable together by a coupling member, said first tube is in communication with said arch cell and said second tube is in communication with said tendon cell.

47. The sleeve assembly of claim 33 wherein said tendon cell includes first and second lateral self-inflatable compartments separated by a medial non-inflatable portion.

* * * * *